United States Patent [19]
Volante et al.

[11] Patent Number: 4,835,276
[45] Date of Patent: May 30, 1989

[54] PREPARATION OF N-FORMAMIDOYL[(S)-1-T-BUTOXY-3-METHYL-2-AMINO)]1,2,3,4 TETRAHYDROBENZO[b]FURO[2,3-c]PYRIDINE AND DERIVATIVES

[75] Inventors: Ralph P. Volante, East Windsor; Richard Desmond, Highland Park; Ichiro Shinkai, Westfield, all of N.J.

[73] Assignee: Merck & Co., Inc., Rahway, N.J.

[21] Appl. No.: 881,992

[22] Filed: Jul. 3, 1986

[51] Int. Cl.$^4$ .............. C07D 491/048; C07D 491/147; C07D 307/79

[52] U.S. Cl. ........................................ 546/89; 546/62; 549/467

[58] Field of Search ...................... 546/89, 62; 514/285

[56] References Cited

U.S. PATENT DOCUMENTS 4,690,928 9/1987 Huff et al. .......................... 514/285
4,721,787 1/1988 Hutchinson .......................... 546/89

FOREIGN PATENT DOCUMENTS 0154142 1/1985 European Pat. Off. .
0251714 1/1988 European Pat. Off. .

OTHER PUBLICATIONS

Loewe and Meyers, "An Asymmetric Synthesis of Indole Allcenloids", Tetrahedron Letters, vol. 26 No. 28 p. 3293 (1985).
Meyers, "Formamidines as Precursors to α-Amino Carbanions & Their Appl. to Asymm. C-C Bond-Forming Reactions", Aldrich. Act., vol. 18, No. 3 (1985).

Primary Examiner—Donald G. Daus
Assistant Examiner—Andrew G. Rozycki
Attorney, Agent, or Firm—William H. Nicholson; Michael C. Sudol, Jr.

[57] ABSTRACT

The present invention is directed to an enantioselective synthesis of 1,3,4,6,7,12b(S)-hexahydro-2H-benzo[b]furo[2,3-a]quinolizin-2-one which is an intermediate in the production of the $\alpha_2$-adrenergic antagonist (2R,12bS)-N-(1,3,4,6,7,12-hexahydro-2H-benzo[b]furo[2,3-a]quinolizin-2-yl)-N-methyl-2-hydroxyethanesulfonamide hydrochloride.

1 Claim, No Drawings

PREPARATION OF N-FORMAMIDOYL[(S)-1-T-BUTOXY-3-METHYL-2-AMINO)]1,2,3,4 TETRAHYDROBENZO [B]FURO [2,3-C]PYRIDINE AND DERIVATIVES

BACKGROUND OF THE INVENTION

Published European Patent Application No. 154,142, and U.S. application Ser. No. 755,863, now abandoned, filed July 17, 1985 which are incorporated herein by reference, disclose the compound (2R,12bS)-N-(1,3,4,6,7,12-hexahydro-2H-benzo[b]furo[2,3-a]-quinolizin-2-yl)-N-methyl-2-hydroxyethanesulfonamide and the quinolizin-2-one intermediate and alternate routes for their synthesis. With the present invention there is provided a new enantioselective route for the synthesis of the intermediate.

The quinolizin-2-one intermediate was previously prepared by standard chemical resolution of racemic ketoamine with L-(+)di-p-toluoyl tartaric acid to give (−)12b(S)ketoamine in 30–35% yield. A resolution process has a maximum yield of 50%, thus one must always lose 50–65% of the total racemic material being resolved. The present invention produces 12b(S)ketoamine of greater than 90% optical purity, with optimization to 99% optical purity possible. This invention obviates the need for chemical resolution and, thus, provides a more efficient synthesis of the (−)-12b(S)ketoamine.

DESCRIPTION OF THE INVENTION

The novel process of this invention is an enantioselective process for the preparation of 1,3,4,6,7,12b(S)-hexahydro-2-H-benzo[b]furo[2,3-a]quinolizin-2-one, comprising:

(A) heating a tricyclic amine of structural formula

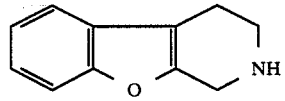

in an aromatic solvent such as benzene, toluene, or the like at about 60° C. to reflux temperature for 8 to 24 hours with a formamidine of structure:

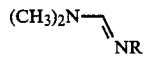

wherein R is:

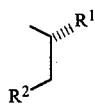

wherein $R^1$ is a:
  (i) straight or branched $C_1$–$C_5$ alkyl, or
  (ii) phenyl, either unubstituted or substituted with $C_1$–$C_3$ alkyl, $C_1$–$C_3$ alkoxy, or halo such as fluoro or chloro; and
wherein $R^2$ is a:
  (i) $C_1$–$C_5$ alkoxy,
  (ii) phenoxy, either unsubstituted or substituted with $C_1$–$C_3$ alkyl, $C_1$–$C_3$ alkoxy, or halo such as fluoro or chloro,
  (iii) tri($C_1$–$C_5$ alkyl)silyloxy,
  (iv) $C_1$–$C_5$ alkylthio,
  (v) di($C_1$–$C_5$ alkyl)amino,
  (vi) phenylthio, either unsubstituted or substituted with $C_1$–$C_3$ alkyl, $C_1$–$C_3$ alkoxy or halo, such as fluoro or chloro,
  (vii) di(phenyl)amino, wherein the phenyl groups can be unsubstituted or substituted with $C_1$–$C_3$ alkyl, $C_1$–$C_3$ alkoxy or halo, such as fluoro or chloro, to form an amidine of the structure:

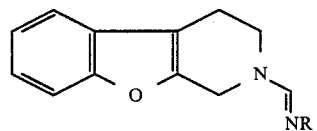

wherein R is as defined above, (B) treating the amidine from Step A in an ethereal solvent such as THF, diethyl ether, 1,2-dimethoxyethane or the like at about −100° C. to −50° C. for about 1–4 hours in the presence of a strong base such as lithium diisopropylamide or alkyllithium, with an alkyl halide of the formula:

$$R^3CH_2X$$

wherein X is halogen (chloro, bromo or iodo), and $R^3$ is —C≡CH, —C(CH_2)Y wherein Y is halo, or —OR$^4$ wherein $R^4$ is tri($C_1$–$C_5$ alkyl)silyl, $C_1$–$C_3$ alkyl or phenyl, to form the compound of structural formula:

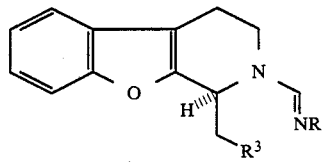

wherein R and $R^3$ are as defined above;

(C) treating the product from Step (B) with hydrazine and acetic acid in an aqueous $C_{1-3}$ alkanol at about 50°–110° C. for about ½ to 3 hours to form the free amine of structural formula:

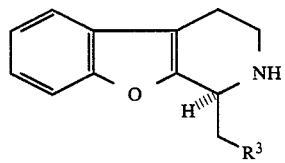

wherein $R^3$ is as defined above, which is extracted from the solution;

(D) heating the extracted product of Step (C) with formaldehyde, or formaldehyde precursor such as paraformaldehyde, and aqueous acid at about 50° to 100° C. for about 12 to 20 hours to form the compound of structural formula:

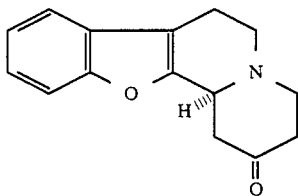

EXAMPLE 1

(2R,12bS)-N-(1,3,4,6,7,12b-hexahydro-2H-benzo[b]-furo[2,3-a]quinolizin-2-yl)-N-methyl-2-hydroxyethanesulfonamide hydrochloride Step A: Preparation of 3-Cyanomethylbenzo[b]furan

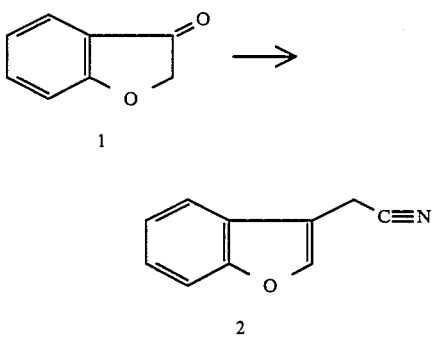

To a suspension of 27 gms (1.12 mole) of oil free sodium hydride in 400 ml of tetrahydrofuran (THF) was added dropwise a solution of 199.2 gms (1.12 mole) of diethylcyanomethylphosphonate in 400 mL of THF. After the H$_2$ evolution had ceased, a solution of 150.1 g (1.12 mole) of 3-(2H)-benzo[b]-furanone in 1 L of THF was added. The solution was heated at 70° C. for 1.5 hours, cooled, and poured into 500 mL of 5% HCl, and washed with ether. The ether phase was washed with brine, dried (MgSO$_4$), filtered and concentrated to give 15.4 g of a dark oil. The product was distilled at 110°–120° C./0.7 Torr Hg to give 116 g (66% yield) of a yellow oil which crystallized upon standing.

Step B: Preparation of 2-(3-benzo[b]furanyl)ethylamine

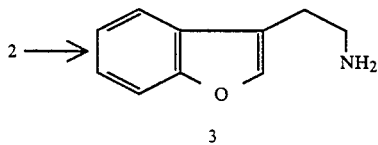

To a solution of 3.1 g of 3-cyanomethylbenzo[b]furan in 40 mL of methanol was added 2.4 g of Raney nickel. The reaction was agitated at 25° C. in a Parr apparatus under 40 psi hydrogen for 2½ hours. The suspension was filtered through a pad of filter aid and the filtrate was evaporated to give 2.2 g (71% yield) of oily product.

Step C: Preparation of 3-(2-Formamidoethyl)benzo[b]furan

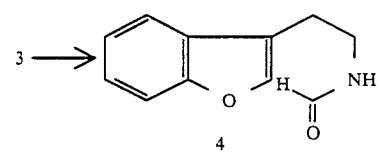

A solution of 121 g of 2-(3-benzo[b]furanyl)-ethylamine and 300 mL of ethyl formate was heated at 60° C. for 3 hours, poured into 2N HCl and washed with methylene chloride which in turn was washed with 5% sodium hydroxide (w/v), dried (Na$_2$SO$_4$), charcoaled and concentrated to give 118 g of product.

Step D: Preparation of 3,4-dihydrobenzo[b]furo-[2,3-c]pyridine

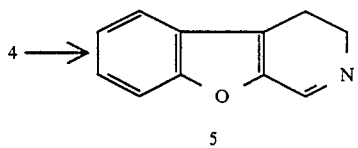

94 Grams of 3-(2-formamidoethyl)benzo[b]-furan was added to 70.5 g of polyphosphoric acid in 477 mL of methane sulfonic acid which was preheated to 90° C. After 2 hours at 85°–90° C., the reaction mixture was poured into 500 mL of water maintaining the temperature below 50° C. The polyphosphoric acid was dissolved in water, filtered through a pad of celite and made basic with concentrated ammonia. A precipitate was collected and dried to give 47.5 g (92% yield) of a tan colored solid product, m.p. 170°–171° C.

Step E: Preparation of 1,2,3,4-tetrahydro-benzo[b]-furo[2,3-c]pyridine

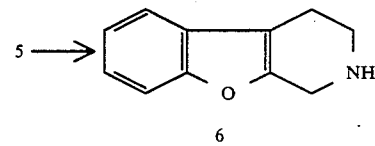

10.0 g of 3,4-dihydrobenzo[b]furo[2,3-c]pyridine was dissolved in 300 ml of tetrahydrofuran and 5 ml acetic acid and treated with 1 g of 5% palladium on carbon catalyst at 22°–24° C. with 40 psi of hydrogen for 16 hours. The catalyst was removed by filtration and the solvent was removed in vacuo to give a tan solid. The solid was suspended in methylene chloride and washed with aqueous ammonium hydroxide. The methylene chloride layer was dried over sodium sulfate and concentrated in vacuo to give the tricyclic amine (8.37 g 83%).

Step F: Preparation of N-formamidoyl[(S)-1-t-butoxy-3-methyl-2-amino]1,2,3,4-tetrahydrobenzo[b]-furo[2,3-c]pyridine

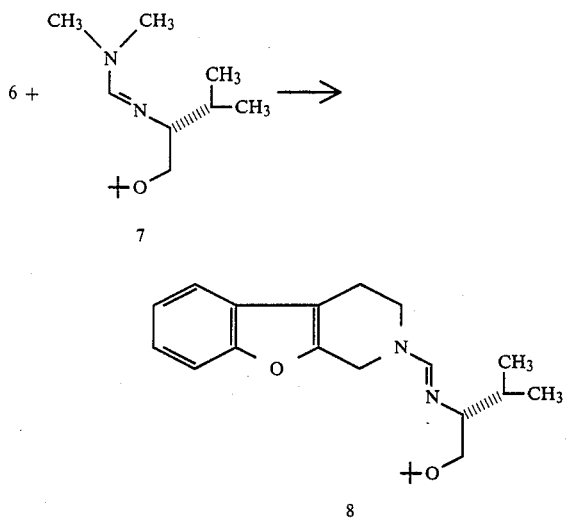

1.33 g of the tricyclic amine of Step E was treated with the formamidine, 7, in 11 ml of toluene at reflux temperatures (105°–110° C.) for 16 hours. The mixture was concentrated in vacuo to remove toluene and chromatographed over E. Merck silica gel 60, 70–230 mesh, eluting with ethyl acetate. Concentration of the rich cut fractions gave 2.51 g of t-butylvalinol derived formamidine (95%).

Step G: Preparation of 12b(S) 3-(2-bromo-1-propenyl)-1,2,3,4-tetrahydrobenzo[b]furo[2,3-c]pyridine

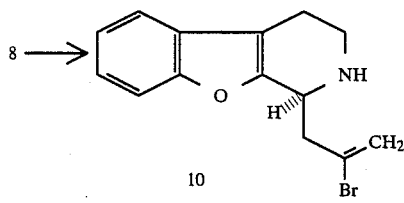

The formamidine of Step F (95 mg, 0.278 mmol) was dissolved in 12.5 ml of tetrahydrofuran and added to 0.33 mmol of lithium diisopropylamide in 1.5 ml of tetrahydrofuran at −78° C. The reaction mixture was stirred at −78° C. for 2 hours and 1,2-dibromopropane (80 mg, 0.39 mmol) was added via syringe. The mixture was stirred at −78° C. for 1 hour and quenched with 10 ml H₂O and warmed to 22°–24° C. The solution was extracted with methylene chloride and the organic phase was dried over sodium sulfate and concentrated in vacuo to give 125 mg of crude formamidine, which in turn was treated directly with 40 microliters of hydrazine hydrate and 50 μl of acetic acid in 2 ml of 60% aqueous ethanol at 80° C. for 1.5 hour. The mixture was cooled to 22°–24° C. and diluted with 20 ml H₂O. The aqueous mixture was extracted with methylene chloride, dried over sodium sulfate, and concentrated in vacuo to give 65 mg of amino compound (78% yield). NMR analysis showed the amine to be a 96:4 mixture of 12b(S) to 12b(R) enantiomers.

Step H: 1,3,4,6,7,12b(S)-hexahydro-2H-benzo[b]furo-[2,3-a]quinolizin-2-one(11)

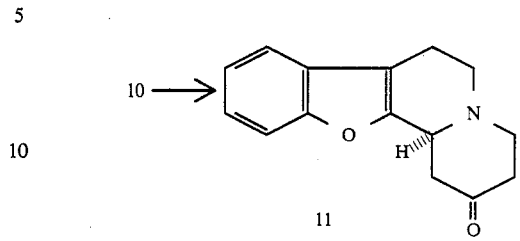

300 mg of vinyl bromo-amine 10 was heated in 10 ml of a mixture of 60% aqueous acetic acid: methanol (1:1) at 65°–70° C. and 300 mg of paraformaldehyde was added. The mixture was then stirred under $N_2$ at 65°–70° C. for 16 hours. The reaction mixture was cooled to 22°–24° C. and diluted with 25 ml of water and made basic by the addition of saturated potassium carbonate solution (pH 12). The aqueous phase was then extracted with 50 ml of ethyl acetate and the organic phase was dried over magnesium sulfate and concentrated in vacuo to give 205 mg of keto-amine 11 as a tan solid (85% yield). $[\alpha]25° - 83.3°$ (C in).

Step I: Preparation of (2SR,12bRS)-N-(1,3,4,6,7,12b-hexahydro-2H-benzo[b]furo[2,3-a]quinolizin-2-yl)-N-methylamine

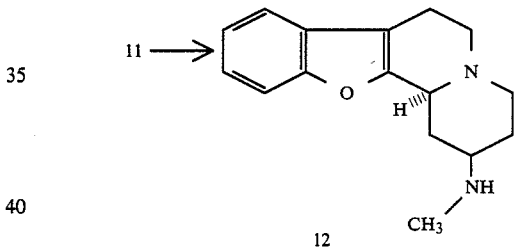

To a solution of 25.5 g (0.106 mol) of (12bRS)-1,3,4,6,7,12b-hexahydrobenzo[b]furo[2,3-a]-quinolizin-2-one dissolved in 360 mL of ether and 210 mL of benzene cooled to −10° C. in an ice-acetone bath was added 22.8 g (26.7 mL, 0.74 mol) methylamine followed by a solution of 10.2 g (5.93 mL, 0.054 mol) of titanium tetrachloride in 25 mL of benzene. The reaction was stirred at −10° to 0° C. for 30 minutes, warmed to 25° C. and stirred 2 hours. The mixture was filtered through a pad of celite, and the salts were washed with benzene/ether (2:1). The filtrate was concentrated to dryness and the residue was dissolved in 700 mL of absolute ethanol and 4.47 g (0.125 mol) of sodium borohydride was added. The solution was stirred 18 hours at room temperature, and 500 mL of water was added. Stirring was continued for 30 minutes; the ethanol was evaporated in vacuo and the aqueous phase was extracted with methylene chloride which was dried ($Na_2SO_4$), filtered, and concentrated, giving 28.8 g of product. The material was recrystallized from 300 mL of ethanol/water (1:1) to give 21.3 g of colorless crystals which analyzed as the 2.5 hydrate. The crystals were dissolved in methylene chloride and dried ($Na_2SO_4$). Evaporation of the solvent yielded 20.5 g of product, m.p. 77–79 C., $[\alpha]_D = 71°$ (C=1 in $CHCl_3$).

Step J: Preparation (2R,12bS)-N-(1,3,4,6,7,12-Hexahydro-2H-benzo[b]furo[2,3-a]quinolizin-2-yl)-N-methyl-2-hydroxyethanesulfonamide

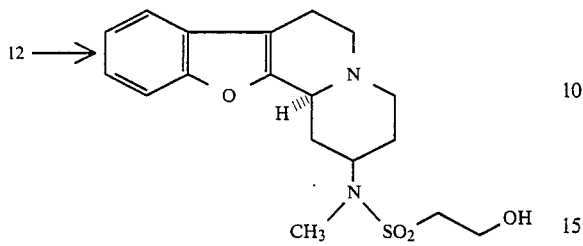

Solutions of 2-hydroxyethanesulfonyl chloride (20.2 g; 0.14 mol) in 100 mL of CH₃CN and (C₂H₅)₃N (14.3 g; 19.7 mL; 0.14 mol) in 100 mL of Ch₂Cl₂ were added simultaneously by means of a dual syringe drive to a solution of 9 (17.9 g; 0.07 mol) in 1600 mL of a 1:1 mixture of CH₃CN and CH₂Cl₂. After 15 minutes the solvent was evaporated and the residue partitioned between CH₂Cl₂ and H₂O. The organic phase was separated and washed with H₂O, brine, and dried (Na₂SO₄). The solvent was evaporated and the residue chromatographed over silica gel, eluting with CHCl₃ saturated with NH₃. The product obtained (14 g; 55%) was converted to the hydrochloride salt by adding C₂H₅OH—HCl to a solution of the base in ethyl acetate. There was obtained 14 g of the product: mp 270°–272° C.; [α]D=13° (C=0.1 $_m$CH₃OH).

Steps A, B, C, D, I and J are disclosed in published European Patent Application No. 154,142 and U.S. application Ser. No. 755,863, filed July 17, 1985, the disclosures of which are incorporated herein by reference.

What is claimed is:

1. A compound of structural formula:

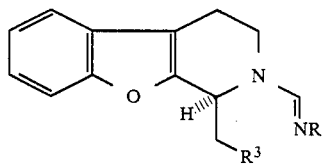

wherein R is:

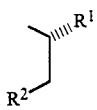

wherein $R^1$ is 2-propyl, $R^2$ is t-butoxy, $R^3$ is —C(=CH₂)X and X is bromo.

* * * * *